US005626881A

United States Patent [19]
Lown

[11] Patent Number: 5,626,881
[45] Date of Patent: May 6, 1997

[54] HUMATE DIETARY SUPPLEMENT

[75] Inventor: John F. Lown, Dallas, Tex.

[73] Assignee: Menefee Mining Corporation, Dallas, Tex.

[21] Appl. No.: 442,333

[22] Filed: May 16, 1995

[51] Int. Cl.$^6$ .................................................. A61K 35/12
[52] U.S. Cl. ............................ 424/520; 424/537; 424/543; 514/125; 514/960; 514/904; 514/905
[58] Field of Search ........................ 424/489, 499, 424/520, 537, 543; 514/125, 195.1, 960, 961, 904, 905

[56] References Cited

U.S. PATENT DOCUMENTS

| | | | |
|---|---|---|---|
| 1,355,732 | 10/1920 | Bottomley. | |
| 2,178,051 | 10/1939 | Sams | 71/8 |
| 2,926,085 | 2/1960 | Geerlings | 99/2 |
| 3,544,296 | 12/1970 | Karcher | 71/24 |
| 3,950,546 | 4/1976 | Hill et al. | 426/72 |
| 4,225,592 | 9/1980 | Lakatos et al. | 424/180 |
| 4,322,443 | 3/1982 | Frontczak | 426/28 |
| 4,380,551 | 4/1983 | Frontczak | 426/28 |
| 5,026,416 | 6/1991 | Alexander | 71/24 |
| 5,411,569 | 5/1995 | Hjersted | 71/24 |
| 5,501,857 | 3/1996 | Zimmer | 424/438 |

OTHER PUBLICATIONS

Corson, "Chickens", *Research Conducted by Intertec, Inc.*, pp. 1–4, 1976.

*Primary Examiner*—James J. Seidleck
*Assistant Examiner*—Michael Williamson
*Attorney, Agent, or Firm*—Baker & Botts, L.L.P.

[57] ABSTRACT

Humate, a composition of primarily humic acids, carbon, and organic matter, is used as a human dietary supplement. The humate may be mixed with food, liquid drinks, or flavoring and ingested. The powder, granule, or water-soluble powder form of humate may also be mixed with other known dietary supplements such as multi-vitamins and be formed into capsules and tablets. The preferred humate is mined from the Menefee Geological Formation in Northwestern New Mexico.

28 Claims, No Drawings

HUMATE DIETARY SUPPLEMENT

TECHNICAL FIELD OF THE INVENTION

This invention is related in general to the field of dietary supplements. More particularly, the invention is related to a humate dietary supplement for the promotion of nutrient absorption and the method for making thereof.

BACKGROUND OF THE INVENTION

Humate is an highly compressed prehistoric compost that can be mined from deposits in the ground. Humate is composed of mainly humic acid, carbon, and some organic matter. A specific humate, also called Menefee Humate™, has a sand and diatomaceous earth base rather than a clay base found in leonardite. The Menefee Humate™ is mined in the area around the Menefee Geological Formation in Northwestern New Mexico by Menefee Mining Corporation of Dallas, Tex. The Menefee Humate™ is a freshwater humate consisting of decomposition of tropical prehistoric plant and animal material. In contrast, other humates are saltwater humates originated from ancient peat bogs.

Humate has been commercially used as a turf and agricultural fertilizer additive. For example, U.S. Pat. No. 3,544,296 issued to Karcher teaches a method for making a soil nutrient from leonardite, and U.S. Pat. No. 5,026,416 issued to Alexander teaches a liquid crop stimulant using humic acid and either calcium phosphate or ascorbic acid. Additionally, certain mineral and clay compositions have been used as an animal feed supplement. For example, U.S. Pat. No. 3,950,546 issued to Hill et al. teaches a mixture of clay having aluminum silicate and sodium bentonite in combination with minerals for spreading on farrow house floors. U.S. Pat. No. 2,926,085 issued to Geerlings suggests mixing mineral salts with humus and colloidal clay as a anemia preventative for newborn pigs.

Peat is also known in the art as an ingredient for soil preparation and animal feed. For example, U.S. Pat. Nos. 4,380,551 and 4,322,443 issued to Frontczak teach a method for preparing a foodstuff for human and animal consumption by sowing seeds in peat, and then recovering the germinated seeds and the peat as the foodstuff. Another patent, U.S. Pat. No. 2,178,051, is directed to a method of treating peat for the purpose of drying it quickly so as to make it suitable as a manure or fertilizer or as an ingredient for animal feed.

SUMMARY OF THE INVENTION

In accordance with the present invention, a human dietary supplement is provided which provides improved digestive process and better nutrient absorption.

In one aspect of the invention, the dietary supplement includes the humate having a level of at least 30% humic acids. The humate is ingested either alone or in combination with food, vitamins, or other dietary supplement ingredients.

In another aspect of the invention, measured amounts of the humate is encapsulated or formed into tablets or pills for ease of human consumption. The humate may also be mixed with flavorings, vitamins, or other dietary supplement ingredients prior to being formed into capsules and pills.

In yet another aspect of the invention, the dietary supplement includes at least 35% humic acids, 35% carbon, and other organic matter.

In another aspect of the invention, the dietary supplement includes a form of water-soluble humate powder that is added to water and ingested alone or in combination with other liquids, nutrients, and/or flavorings.

DETAILED DESCRIPTION OF THE INVENTION

Most humate-type organic deposits are found buried in the earth's crusts, similar to coal deposits. Unlike lignite coal based humates, such as leonardite, that have a clay base, the Menefee Humate™ has a sand and diatomaceous earth base. The sand and diatomaceous earth ($SiO^2$) base of this humate resisted compression and allowed air and water movement throughout the formation of the humate. Unlike lignite deposits, the Menefee deposits were not subjected to the high pressure and lack of oxygen conditions which formed the lignite deposits. The primary constituents of humate are humic acids, carbon, and organic matter. The detailed analysis of the composition of the Menefee Humate™ is shown below:

| Minimum Analysis (%) | |
|---|---|
| Humic Acid | 35.0 |
| Organic Matter | 35.0 |
| Nitrogen | 0.88 |
| Phosphoric Acid | 0.07 |
| Potash | 0.06 |
| Manganese | 0.02 |
| Zinc | 0.008 |
| Copper | 0.001 |
| Iron | 0.59 |
| Sodium | 0.03 |
| Potassium | 0.037 |
| Calcium | 0.45 |
| Magnesium | 0.07 |
| Phosphorus | 0.02 |
| Sulfer | 0.14 |
| Lead | 0.002 |
| Chromium | <0.002 |
| $SiO^2$ | 19.1 |
| $Al^2O^2$ | 5.5 |
| Boron | 0.02 |
| Gold | <0.001 |
| Carbon | 35.0 |

Another chemical analysis shows the following composition of the humate:

| Analysis | Level Found | Method |
|---|---|---|
| Humic Matter % | 60.8 | COM SSPA 15(12)84 |
| OM by Combustion % | 71.50 | 550° C. |
| Sulfate Sulfer % ($So_4$—S) | 0.27 | AOAC 15th Ed. 957.02e/ICP |
| Phosphorus % (P) | 0.02 | AOAC 15th Ed. 957.02e/ICP |
| Potassium % (K) | Not Detected | AOAC 15th Ed. 957.02e/ICP |
| Magnesium % (Mg) | 0.16 | AOAC 15th Ed. 957.02e/ICP |
| Calcium % (Ca) | 0.43 | AOAC 15th Ed. 957.02e/ICP |
| Sodium % (Na) | 0.14 | AOAC 15th Ed. 957.02e/ICP |
| Iron % (Fe) | 0.347 | AOAC 15th Ed. 957.02e/ICP |
| Manganese % (Mn) | 0.002 | AOAC 15th Ed. 957.02e/ICP |
| Copper % (Cu) | 0.003 | AOAC 15th Ed. 957.02e/ICP |
| Zinc % (Zn) | 0.004 | AOAC 15th Ed. 957.02e/ICP |
| Aluminum % (Al) | 0.57 | AOAC 15th Ed. 957.02e/ICP |

-continued

| Analysis | Level Found | Method |
|---|---|---|
| Ignitability °F. | >430 | ASTM D 92 Mod |
| Moisture % | 13.50 | AOAC 15th Ed. 965.08 |

Although this invention is directed to a dietary supplement incorporating humate or humic acids, the preferred origin for the humate or humic acids is from the Menefee Geological Formations in Northwestern New Mexico.

Humic acid, defined as the portion of soil humus that is soluble in alkaline solution, but insoluble in acid solution, is the form of organic matter that often is added to the soil to increase fertility. Humic acids are found in rotting vegetable matter and can be detected in the black slime of an ordinary compost pit in a home garden. It also is found in the brown organic matter of a variety of soils, as well as in peats, manure, lignite, leonardite, brown coals, and the Menefee Humate™. Humic acids do not have a single unique structure, but are a mixture of intermediate chemical products resulting from the decomposition and conversion of lignin and other plant materials to hard coal. Humic acids apparently are formed by the bacterial and chemical degradation of plant tissue, but in soils it also may be formed by certain secondary processes such as polymerization of polyphenols leached by rain from surface leaf litter, and condensation of phenols, quinones, and proteins that are provided by the action of soil micro-organisms and small animals on soil carbohydrates. As a result, humic acid is best characterized in terms of its origin and soil environment, rather than in rigid terms of chemical composition or chemical properties.

Chemical studies of the composition of humates such as Menefee Humate™ and leonardite have revealed that it is mainly composed of the mixed salts of acid radicals found in soil humus, a product of the decay of organic matter that contains both humic and nonhumic material. Such acid radicals are collectively termed "humic acids," having individual factions named humin, humic acid, ulmic acid and fulvic acid. The exact structure of the humic acids are unknown. However, humic acids appear to be associations of molecules forming aggregates of elongated bundles of fibers at low pH, and open flexible structures perforated by voids at high pH. These voids, of varying dimensions, trap organic or inorganic particles of appropriate electronic charge.

The humic acids have a large cation exchange capacity and hold multivalent metallic elements, such as micronutrient elements, very strongly. The molecular weight of the humic acids range from 800 to 500,000, with the weight average molecular weight ranging from about 5,000 to about 50,000. The cation exchange capacity of the humic acids varies from about 200 to about 600 meq $CaCO_2$ per 100 grams at pH 7, depending upon the origin of the extracted acids. Humic acids are polyelectrolytes and are believed to form complexes with clay particles thus enabling humic acids to bind multivalent elements with great tenacity. When the cation exchange sites on the humic acid molecule are filled predominantly with hydrogen ions, the material, considered to be an acid, is insoluble in water. However, when the predominant cations at the exchange sites are other than hydrogen, the material is called a "humate." Humates of monovalent alkali metals or ammonia are soluble in water, but the humates of most multivalent metals are insoluble.

It has been shown in studies done on poultry, livestock and other animals that the addition of a humate-like material to the feed promotes growth, better health, and decreased mortality rates. Humic acids have negatively charged ionic sites which singly or in combination chelate or attract and hold positively charged ions and molecules. The carbon chains of the organic matter provide an energy source (food) for microbes which increases their number dramatically. The microbes release enzymes which etch metallic ions or fracture molecules from the food the animal eats which is captured by the humic acids and expedited through the digestive system into contacted cells.

There are three known ways humic acids or humates affect ionic molecular uptake. First, a direct interaction between the humate and cell membrane responsible for ionic transfer. Second, humic acids changes the membranes passive permeability allowing greater ion contact and transfer to cellular proteins. And finally, indirect effects, caused by humic acids, can affect transport through changes in the metabolic processes regulating uptake. There is also evidence that intake of humate or humic acid bolsters the immune system and decreases the incidence of illness due to pathogens such as salmonella and *e coli*.

The Menefee Humate™ is a sand and diatomaceous earth-based granular or powdered material that has a low moisture content. This dry granule or powder is readily mixable with food or liquid drinks for human consumption. The slightly earthy taste of the humate may also be enhanced or masked by flavoring of various kinds. The granules or water-soluble powder can also be mixed with multivitamins, trace elements, and other dietary supplement ingredients. Further, the Menefee Humate™ can be easily encapsulated into capsules or formed into tablets and pills either alone or in combination with vitamins or other diet supplement ingredients to facilitate ingestion by humans. The daily recommended intake amount will be dependent on an individual's requirements, but may range from 1 to 5 grams, dependent on age, weight, and overall health condition.

Although the present invention and its advantages have been described in detail, it should be understood that various changes, substitutions and alterations can be made therein without departing from the spirit and scope of the invention as defined by the appended claims.

What is claimed is:

1. A human dietary supplement, comprising:

a humate of prehistoric origin;

some carbon;

some organic matter; and a mixture of said humate, carbon, and organic matter being made for human ingestion.

2. The dietary supplement human, as set forth in claim 1, wherein said humate comprises at least 35% humic acids.

3. The dietary supplement human, as set forth in claim 1, comprising at least 35% carbon.

4. The dietary supplement human, as set forth in claim 1, comprising at least 35% organic matter.

5. The dietary supplement human, as set forth in claim 1, further comprising vitamins.

6. The dietary supplement human, as set forth in claim 1, further comprising trace elements.

7. The dietary supplement human, as set forth in claim 1, wherein the dietary supplement is in granule form.

8. The dietary supplement human, as set forth in claim 1, wherein the dietary supplement is in powder form.

9. The dietary supplement human, as set forth in claim 1, wherein the dietary supplement is in solution in water or in a liquid drink.

10. A human dietary supplement, comprising:
at least 35% humic acids of prehistoric origin;
at least 35% carbon;
some organic matter; and
said humic acid, carbon, and organic matter being mixed together for human ingestion.

11. The human dietary supplement, as set forth in claim 10, comprising at least 35% organic matter.

12. The human dietary supplement, as set forth in claim 10, further comprising vitamins.

13. The human dietary supplement, as set forth in claim 10, further comprising trace elements.

14. The human dietary supplement, as set forth in claim 10, wherein the human dietary supplement is in granule form.

15. The human dietary supplement, as set forth in claim 10, wherein the human dietary supplement is in powder form.

16. The human dietary supplement, as set forth in claim 10, wherein the human dietary supplement is in solution in water or in a liquid drink.

17. A method for supplementing human diet, comprising the steps of:
mixing a predetermined weight of humate of prehistoric origin having at least 30% humic acids with one or more known human dietary supplement ingredients; and
ingesting the mixture.

18. The method, as set forth in claim 17, further comprising the step of encapsulating the mixture into a capsule.

19. The method, as set forth in claim 17, further comprising the step of forming the mixture into a pill.

20. The method, as set forth in claim 17, further comprising the step of:
measuring a predetermined amount of the mixture; and
combining the mixture with a food or liquid drink.

21. The method, as set forth in claim 17, further comprising the step of grinding a humate in granule form into a water-soluble powder.

22. The method, as set forth in claim 17, wherein the mixing step includes the step of mixing the humate with nutrients, including trace elements or vitamins.

23. The method, as set forth in claim 21, further comprising the step of mixing the water-soluble powder with water or a liquid drink.

24. The method, as set forth in claim 21, wherein the water-soluble powder is mixed with nutrients, including vitamins.

25. The human dietary supplement, as set forth in claim 1, wherein a significant percentage of said humate is obtained by mining.

26. A human dietary supplement, as set forth in claim 1, wherein a significant percentage of said humate is obtained by mining from the Menefee geological formation located in northwest New Mexico.

27. The human dietary supplement, as set forth in claim 10, wherein a significant percentage of said humic acids are obtained by mining.

28. The method, as set forth in claim 17, further comprising the step of obtaining a significant portion of said humate by mining.

* * * * *